(12) United States Patent (10) Patent No.: US 12,636,660 B2

Kim (45) Date of Patent: May 26, 2026

(54) GRAVEL CIRCULATION DRY ELECTROSTATIC PRECIPITATOR

(71) Applicant: METRO ENGINEERING CO., LTD., Incheon (KR)

(72) Inventor: Kyeong Joon Kim, Gyeonggi-do (KR)

(73) Assignee: METRO ENGINEERING CO., LTD., Incheon (KR)

( * ) Notice: Subject to any disclaimer, the term of this patent is extended or adjusted under 35 U.S.C. 154(b) by 310 days.

(21) Appl. No.: 18/694,029

(22) PCT Filed: Dec. 15, 2022

(86) PCT No.: PCT/KR2022/020417

§ 371 (c)(1),
(2) Date: Mar. 21, 2024

(87) PCT Pub. No.: WO2024/014630

PCT Pub. Date: Jan. 18, 2024

(65) Prior Publication Data

US 2024/0382977 A1      Nov. 21, 2024

(30) Foreign Application Priority Data

Jul. 15, 2022      (KR) ......................... 10-2022-0087303

(51) Int. Cl.
B01J 21/06 (2006.01)
A61L 9/22 (2006.01)
(Continued)

(52) U.S. Cl.
CPC .................................... B03C 3/38 (2013.01); A61L 9/22 (2013.01); B01D 53/32 (2013.01); B01D 53/86 (2013.01); B01J 21/063 (2013.01); B03C 3/04 (2013.01); B03C 3/41 (2013.01); B03C 3/49

(2013.01); B03C 3/66 (2013.01); C04B 18/167 (2013.01); C04B 20/04 (2013.01); B01D 2255/20707 (2013.01); B01D 2257/90 (2013.01);

(Continued)

(58) Field of Classification Search
CPC ....................................................... B03C 3/38
See application file for complete search history.

(56) References Cited

FOREIGN PATENT DOCUMENTS

KR          100779070          11/2007
KR          101485776 B1 *     1/2015     ............... B03C 3/38

OTHER PUBLICATIONS

KR_101485776_B1_Translation (Year: 2015).*

* cited by examiner

*Primary Examiner* — Kevin Joyner
*Assistant Examiner* — Changru Chen
(74) *Attorney, Agent, or Firm* — IPLA P.A.

(57) ABSTRACT

A gravel circulation dry electrostatic precipitator includes: a drying unit (S1) which conveys and uniformly mixes, heats, and dries recycled aggregates, containing a large amount of moisture, among the materials of asphalt-concrete; a first dust collection and purification unit (S2); a second dust collection and purification unit (S3) in which fine dust, remaining after the odor-inducing substances, harmful gases, and dust that have passed through the first dust collection and purification unit (S2) are filtered by a filter, is discharged to the outside by a screw (S) provided at the lower end of a hopper, and a discharge unit (S4) which uses a turbo fan (F) to forcibly suction fresh air that has passed through the second dust collection and purification unit (S3), thereby discharging same via an outlet (400).

6 Claims, 11 Drawing Sheets

(51) Int. Cl.

| | |
|---|---|
| *B01D 53/32* | (2006.01) |
| *B01D 53/86* | (2006.01) |
| *B03C 3/04* | (2006.01) |
| *B03C 3/38* | (2006.01) |
| *B03C 3/41* | (2006.01) |
| *B03C 3/49* | (2006.01) |
| *B03C 3/66* | (2006.01) |
| *C04B 18/167* | (2023.01) |
| *C04B 20/04* | (2006.01) |

(52) U.S. Cl.
CPC .... *B01D 2258/02* (2013.01); *B01D 2259/812* (2013.01); *B01D 2259/818* (2013.01); *B03C 2201/10* (2013.01)

(a)

(b)

(c)

(A)　　　　　　　(B)　　　　　　　(C)

(D)　　　　　　　(E)　　　　　　　(F)

| ARRANGEMENT DISTANCE | DISCHARGE CURRENT (mA) | CURRENT CONSUMPTION (A) | POWER EFFICIENCY (%) |
|---|---|---|---|
| 30 mm | 19.69 | 3.519 | 50.9% |
| 60 mm | 22.75 | 3.954 | 52.3% |
| 90 mm | 22.19 | 3.883 | 52.0% |

GRAVEL CIRCULATION DRY ELECTROSTATIC PRECIPITATOR

BACKGROUND

The present invention relates to a gravel circulation dry electrostatic precipitator for preventing environmental pollution, as one batch apparatus for removing dusts and odor generated during manufacture of ascon, and more particularly, for removing air pollutants or other harmful dusts emitted during a process of producing the ascon through a corona discharge.

In general, ascon (asphalt-concrete) is produced by heating and mixing an aggregate such as gravel or crushed stone, an additive, and asphalt that is a residue of distillation of crude oil, under certain conditions, and is widely used as materials of pavement for various roads and the like.

A process for producing the ascon as above is described in brief as follows.

The ascon is produced through the process for producing the ascon comprising a process, in which an aggregate transferred from a cold bin to a conveyor belt passes through a dryer to remove moisture contained in the aggregate, and the aggregate is heated to a suitable temperature for mixing the aggregate and asphalt oil (AP oil), a process, in which the heated aggregate is adjusted to a suitable particle size while passing through a hot elevator, a hot screen, and a hot bin, and then a process in which the aggregate with the adjusted particle size is introduced into a mixer, and a suitable amount of asphalt oil (AP oil) heated in an asphalt oil storage tank is introduced into the mixer through a weighing tank to be mixed with the aggregate.

The produced ascon is directly loaded into a truck to be shipped to a paving site. The process for producing the ascon is mainly classified into a "storage equipment" for the aggregate and mineral filler, a "drying equipment" such as dryer, a "mixing equipment" in which the heated aggregate is mixed with asphalt, a "dust collecting equipment" for air pollution prevention, an "ascon loading equipment," and the like. All of four processes excluding the "storage equipment" from the main five processes are in close connection with offensive odor/contaminant emission.

A process of treating air contaminants mainly emitted during the process for producing the ascon as above is mainly classified into two process that are ducted emission and fugitive emission.

The ducted emission is a method of emission of contaminants after purification through a certain contamination treatment equipment, and is an emission mainly from a dryer, a hot elevator, a hot screen, a hot bin, and a mixer.

The fugitive emission includes fugitive dusts generated during the processes of loading the truck with the ascon, storing the aggregate in the cold bin or the like, transferring the aggregate, and the like.

That is, the main contaminants are organic fumes generated by volatilization of dust and AP oil, and the process in which the organic fumes that are offensive odor-causing materials are emitted is a process in which the aggregate and the AP oil are mixed in a recycled aggregate dryer, an AP oil storage tank, and a hot mixer, and a process in which the truck is loaded with the produced ascon.

The main contaminants include organic fumes (microdroplets including VOCs when the aggregate having a high temperature and the AP oil are mixed) and ammonia, aldehydes, aromatics and the like that are generated by evaporation of the AP oil at a high temperature.

The offensive odor or contaminants generated during the process for producing the ascon as describe above are the main causes of very severe environmental pollution, and are problematic as follows.

First, most of the contaminants are difficult to identify with naked eyes.

Second, the offensive odor contaminants are discharged not only from a single source but also from various generation sources as being discharged sporadically rather than continuously from open-air facilities and field operations. Unlike other air contaminants, expectations of effects of improvement over removal investments are very low.

Third, the offensive odor contaminants correspond to environmental pollution caused by release of a great many kinds of materials into the air, and exhibit complicated characteristics in many aspects. Thus, there is a problem that the offensive odor contamination is caused by combined properties of many kinds of compounds rather than by a single material.

Fourth, there are problems that it is very difficult to objectively measure, through an analyzer, various offensive odors and pollutants detected in a unit of ppb through human scent receptors, and even if for the same person, the detection of offensive odors may change according to time, place, concentration and components.

However, the deodorization methods shown in Table 2 above have respective advantages and disadvantages, and thus are not perfect. Therefore, the most effective deodorization method has to be selected in consideration of offensive odor-causing materials in offensive odor removing sites, process change, installation area, work line, temperature, humidity, airflow, secondary pollution management measures, fuel usage and the like. However, there are excessive installation costs and management and operation costs, and many difficulties in maintenance and the like.

Accordingly, Korean Patent Application No. 10-2007-37310 entitled "a dust and offensive odor removing device using a dryer of an ascon plant," filed on Apr. 17, 2007, was registered, and the technical substance thereof is as follows.

In claim 1, an ascon plant comprising: a dryer that heats an aggregate discharged from a cold bin; a hot elevator that transfers the aggregate heated in the drier; and a mixer that discharges, through a discharge part, ascon in a state in which an additive and dust, which are supplied from an additive supply device and a dust supply device, respectively, with the aggregate introduced by being selected and transferred in the hot elevator and weighed, are mixed, wherein the dryer comprises an intake fan for a bag filter, which forcibly suctions odor generated inside the mixer to discharge the odor so as to be incinerated in the dryer, the bag filter, which is provided between the mixer and the intake fan for the bag filter and collects dust inside the mixer to introduce the dust into the hot elevator, and a hood which forcibly suctions odor, which is generated when the ascon is discharged through an outlet of the mixer, to discharge the odor to the dryer.

In claim 2, the ascon plant of claim 1, wherein:

the dryer includes an intake fan that suctions air for combusting fuel, and the intake fan forcibly suctions air mixed with offensive odor through the hood."

The prior registered technology as above can remove parts of harmful gases and the like generated from the ascon may be removed, but is problematic in that air pollutants such as formaldehyde, ammonia, hydrogen sulfide, mercaptan, amines, sulfur dioxide, nitrogen oxides, and dioxin, are not effectively removed.

The technology currently the most widely commercialized as a desulfurization process is a wet type limestone-gypsum process using limestone slurry, and otherwise, some dry processes using dry sorbent, activated carbon, etc. are commercialized.

Meanwhile, methods for removing nitrogen oxides include improvement in fossil fuel combustion methods or denitrification of treating flue gas after combustion in order to fundamentally suppress the generation of nitrogen oxide. Among the methods, flue gas denitrification methods are classified into a wet method and a dry method according to whether to adsorb nitrogen oxides into an aqueous solution or not. As the wet method is less economical than the dry method, and requires treatment of secondary pollutants such as water pollution, the wet method is relatively inferior to the dry method. A typical commercialized process of the dry method is selective catalytic reduction (SCR). The selective catalytic reduction is a process of selectively reducing nitrogen oxides in flue gas to nitrogen and water while allowing flue gas and reductant together to flow through a catalyst layer.

However, in these methods for treating air pollutants according to the related art, pollutants are treated while a large amount of flue gas sequentially undergoes two completely different kinds of processes that are desulfurization and denitrification. Accordingly, initial investment costs and operation costs increase, and an optimum process combination of desulfurization and denitrification is required. In addition, discharge of wastewater in the wet method, and the like are pointed out as problems.

Recently, methods for using plasma to remove air pollutants are implemented to improve the problems in the methods for treating air pollutants according to the related art.

However, most of apparatuses and methods for using plasma to treat air pollutants according to the related art have a problem that the overall structure is so complex to increase manufacture costs. And there is a problem that the implementation does not have optimum discharge condition, and thus air pollutants in flue gas is not effectively removed.

SUMMARY OF THE INVENTION

The present invention has been devised to solve the above problems, and objects of the present invention are as follows.

The present invention may be installed in incinerators, boilers, desulfurization equipment, and other microscopic dust and harmful gas removing equipment in various industrial settings. Thus, microscopic dust and harmful gases included in discharged gases, and particularly microscopic dust and harmful gases generated during a process for producing ascon may be removed or minimized using one batch apparatus to prevent environmental pollution.

Another object of the present invention is to use a principle in which ions, radicals, ozone, and the like generated during electric discharge decompose and remove substances such as sulfur dioxide, nitrogen oxide, and dioxin, contained in air pollutants, so that a large amount of air pollutants are rapidly removed.

The present invention for achieving the above objects is to provide

"A gravel circulation dry electrostatic precipitator including: a drying unit S1 that conveys a recycled aggregate, which contains a large amount of moisture, among materials of asphalt-concrete (ascon) by using a bucket elevator 100 to uniformly mix, heat, and dry the aggregate; a first dust collection and purification unit S2 that forcibly suctions odor-inducing substances, harmful gases, and dust, which are generated in the drying unit S1, through a pipe provided on an upper side to collect and purify the odor-inducing substances, the harmful gases, and the dust; a second dust collection and purification unit S3 in which fine dust, remaining after the odor-inducing substances, the harmful gases, and the dust that have passed through the first dust collection and purification unit S2 are filtered by a filter, is discharged to the outside by a screw S provided at a lower end of a hopper; and a discharge unit S4 that forcibly suctions fresh air, which has passed through the second dust collection and purification unit S3, by using a turbo fan F to discharge the fresh air through an outlet 400, wherein the first dust collection and purification unit S2 includes:

a gravel accommodation part 20 including an inlet 200 on one side thereof and a blower fan 201 on the other side, and having an inner circumferential wall surface on which gravel is accommodated; a gravel collecting part 21 disposed on a lower end of the gravel accommodation part 20 and including a discharge valve 210 through which the gravel is replaced; a corona reaction part 22 provided at a center of an upper inner circumferential portion of the first dust collection and purification unit; and an outflow part 23 which is disposed on one side of the gravel accommodation part 20 and through which the purified air flows out, wherein the corona reaction part 22 includes:

a dust collector 220 in which a plurality of dust collecting pipes 221 are accommodated; and a discharge unit 260 including a discharge rod 230 accommodated inside each of the dust collecting pipes 221 of the dust collector 220, discharge tips 240 coupled to a front end of the discharge rod 230 so as to be spaced a constant distance from each other, and a high-voltage applying device 250 configured to apply a voltage to an end of the discharge rod 230, wherein a fixing groove 231 is defined in the discharge rod 230 so that each of fixing rings 232 is fixed to the fixing groove 231, the discharge tip 240 is seated between the fixing rings 232 so that the discharge tip 240 is inserted into the discharge rod 230 so as to be fixed, and the discharge tip 240 is provided in four to be installed to be spaced 75 mm from each other starting from a front end of the discharge rod 230, wherein, in the discharge tip 240, a through-hole 241 into which the discharge rod 230 is inserted passes through the discharge tip 240, an outside of the discharge tip 240 has a sawtooth shape including a sawtooth ridge 242 and a sawtooth trough 243, each of the sawtooth ridge 242 and the sawtooth trough 243 is provided in twelve to be at constant intervals, the sawtooth ridge 242 has a diameter of 16 mm, the sawtooth trough 243 has a diameter of 11 mm, the discharge tip 240 has a whole thickness of 0.8 mm, and auxiliary through-holes 244 are defined in the through-hole 241 to extend to the outside, and are spaced a predetermined distance from each other.

The gravel circulation dry electrostatic precipitator, wherein the odor-inducing substances, harmful gases, and dust generated from the dried recycled aggregate passing through the drying unit S1 is forcibly suctioned into the first dust collection and purification unit S2, and the remaining recycled aggregate is mixed with a new aggregate separately dried by a drying unit S10 at a fixed ratio in a mixing unit M, and then is discharged to the outside by using a truck T.

The gravel circulation dry electrostatic precipitator, wherein the dust collecting pipe 221 has an outside diameter of 76.3 mm, an inside diameter of 74.5 mm, a thickness of 0.9 mm, and a length of 497 mm, wherein a through-hole 241 into which the discharge rod 230 is inserted passes through the discharge tip 240 of the discharge unit 260, and an outside of the discharge tip 240 has a sawtooth shape including a sawtooth ridge 242 and a sawtooth trough 243, wherein each of the sawtooth ridge 242 and the sawtooth trough 243 is provided in twelve to be at constant intervals, the sawtooth ridge 242 has a diameter of 16 mm, the sawtooth trough 243 has a diameter of 11 mm, and the discharge tip 240 has a whole thickness of 0.8 mm.

The gravel circulation dry electrostatic precipitator, wherein a through-hole 241 into which the discharge rod 230 is inserted passes through the discharge tip 240, and the discharge tip 240 has an outer circumferential surface in which recessed portions 245 are defined, wherein the recessed portions 24 each have both ends, and the ends thereof are in contact with each other to have a peak 246 shape.

The gravel circulation dry electrostatic precipitator, wherein the corona reaction part 22 comprises a titanium dioxide $TiO_2$ that is a deodorizing catalyst, wherein the titanium dioxide is activated by electrons and photons generated during corona discharging to generate a hydroxyl radical for removing an odor-inducing substances.

The gravel circulation dry electrostatic precipitator, wherein the deodorizing catalyst is provided by being mixed with a scoria that is a catalyst support, wherein the deodorizing catalyst is absorbed by or carried on the catalyst support."

The present invention as provided above may be installed in incinerators, boilers, desulfurization equipment, and other microscopic dust and harmful gas removing equipment in various industrial settings. Thus, microscopic dust and harmful gases included in discharged gases, and particularly microscopic dust and harmful gases generated during the process for producing ascon may be removed or minimized using one batch apparatus to prevent environmental pollution. In addition, a principle in which ions, radicals, ozone, and the like generated during electric discharge decompose and remove substances such as sulfur dioxide, nitrogen oxide, and dioxin, contained in air pollutants, may be used to rapidly remove a large amount of air pollutants.

In addition, discharge voltages and discharge current values are optimized through the experiments of the shapes of the discharge tips and the distance between the discharge tips to be disposed on the discharge rod. Thus, a correlation between the dust collection efficiency and the power efficiency may be demonstrated, and an optimum specification may be derived to expect an effect of being capable of maximizing the dust collection efficiency.

In addition, according to the present invention, an occurrence of sparks may be greatly reduced to secure operation reliability. Accordingly, due to the reduction in occurrence of the sparks, lifetime of power supply may be increased to expect an effect that the lifetime increases.

In addition, according to the present invention, each of the dust collecting pipes is capable of being separated individually to be cleaned using brush. Accordingly, a cleaning operation may be easily performed to expect an effect that convenience is greatly increased in terms of maintenance.

Although the preferred embodiments of the present invention have been described, it is understood that the present invention should not be limited to these embodiments but various changes and modifications can be made by one ordinary skilled in the art within the spirit and scope of the present invention.

DETAILED DESCRIPTION OF THE INVENTION

Figure 1:
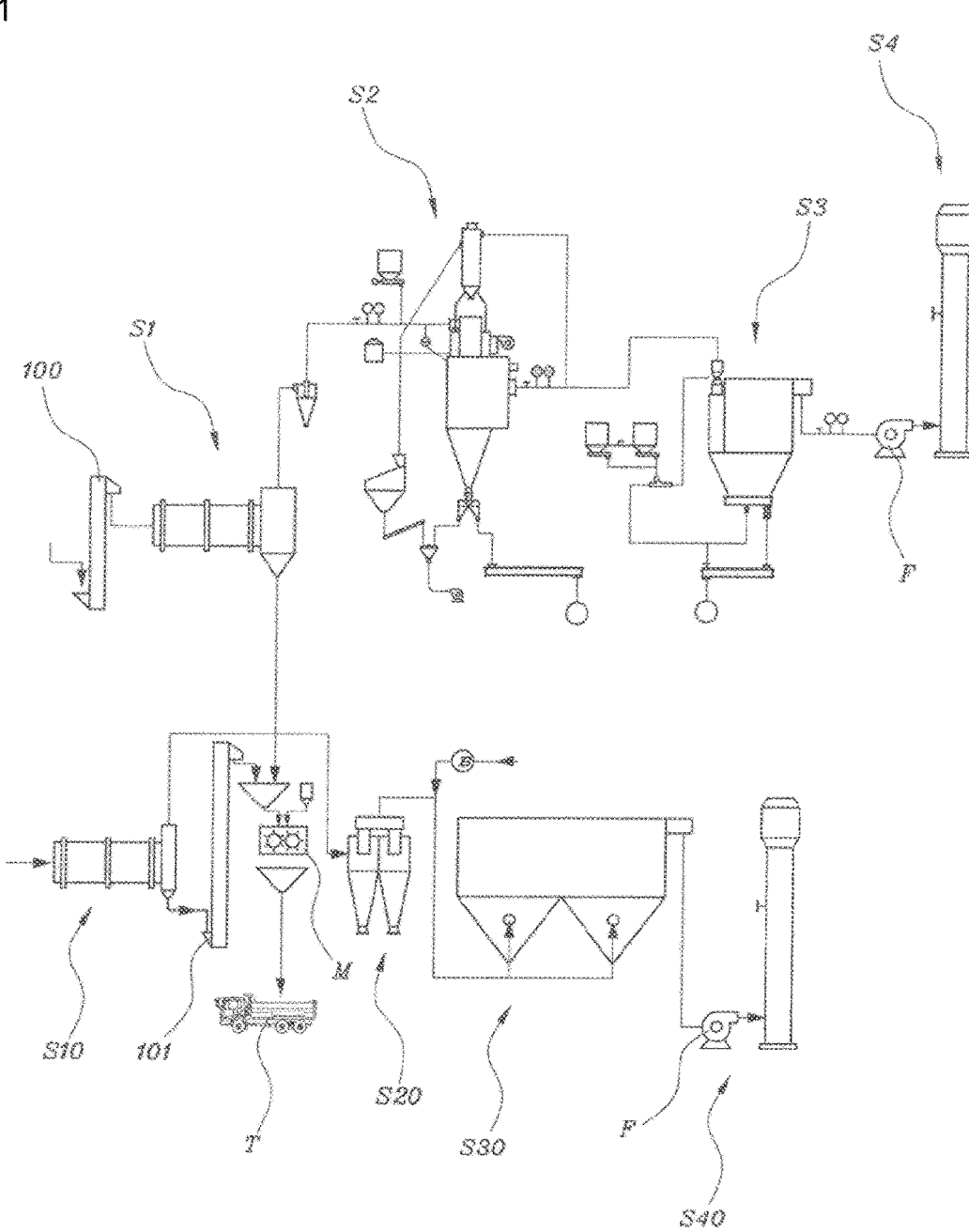
FIG. 1 is an overall schematic view of a gravel circulation dry electrostatic precipitator according to the present invention.

The present invention for achieving the above objects is to provide

"A gravel circulation dry electrostatic precipitator including a drying unit S1 that conveys a recycled aggregate, which contains a large amount of moisture, among materials of asphalt-concrete (ascon) by using a bucket elevator 100 to uniformly mix, heat, and dry the aggregate, a first dust collection and purification unit S2 that forcibly suctions odor-inducing substances, harmful gases, and dust, which are generated in the drying unit S1, through a pipe provided on an upper side to collect and purify the odor-inducing substances, the harmful gases, and the dust, a second dust collection and purification unit S3 in which fine dust, remaining after the odor-inducing substances, the harmful gases, and the dust that have passed through the first dust collection and purification unit S2 are filtered by a filter, is discharged to the outside by a screw S provided at a lower end of a hopper, and a discharge unit S4 that forcibly suctions fresh air, which has passed through the second dust collection and purification unit S3, by using a turbo fan F to discharge the fresh air through an outlet 400, and the first dust collection and purification unit S2 includes a gravel accommodation part 20 including an inlet 200 on one side thereof and a blower fan 201 on the other side, and having an inner circumferential wall surface on which gravel is accommodated, a gravel collecting part 21 disposed on a lower end of the gravel accommodation part 20 and including a discharge valve 210 through which the gravel is replaced, a corona reaction part 22 provided at a center of an upper inner circumferential portion of the first dust collection and purification unit, and an outflow part 23 which is disposed on one side of the gravel accommodation part 20 and through which the purified air flows out, and the corona reaction part 22 includes a dust collector 220 in which a plurality of dust collecting pipes 221 are accommodated, and a discharge unit 260 including a discharge rod 230 accommodated inside each of the dust collecting pipes 221 of the dust collector 220, discharge tips 240 coupled to a front end of the discharge rod 230 so as to be spaced a constant distance from each other, and a high-voltage applying device 250 configured to apply a voltage to an end of the discharge rod 230, and a fixing groove 231 is defined in the discharge rod 230 so that each of fixing rings 232 is fixed to the fixing groove 231, the discharge tip 240 is seated between the fixing rings 232 so that the discharge tip 240 is inserted into the discharge rod 230 so as to be fixed, and the discharge tip 240 is provided in four to be installed to be spaced 75 mm from each other starting from a front end of the discharge rod 230, and in the discharge tip 240, a through-hole 241 into which the discharge rod 230 is inserted passes through the discharge tip 240, an outside of the discharge tip 240 has a sawtooth shape including a sawtooth ridge 242 and a sawtooth trough 243, each of the sawtooth ridge 242 and the sawtooth trough 243 is provided in twelve to be at constant intervals, the sawtooth ridge 242 has a diameter of 16 mm, the sawtooth trough 243 has a diameter of 11 mm, the discharge tip 240 has a whole thickness of 0.8 mm, and auxiliary through-holes 244 are defined in the through-hole 241 to extend to the outside, and are spaced a predetermined distance from each other.

The gravel circulation dry electrostatic precipitator, in which the odor-inducing substances, harmful gases, and dust generated from the dried recycled aggregate passing through the drying unit S1 is forcibly suctioned into the first dust collection and purification unit S2, and the remaining recycled aggregate is mixed with a new aggregate separately dried by a drying unit S10 at a fixed ratio in a mixing unit M, and then is discharged to the outside by using a truck T.

The gravel circulation dry electrostatic precipitator, in which the dust collecting pipe 221 has an outside diameter of 76.3 mm, an inside diameter of 74.5 mm, a thickness of 0.9 mm, and a length of 497 mm, and a through-hole 241 into which the discharge rod 230 is inserted passes through the discharge tip 240 of the discharge unit 260, an outside of the discharge tip 240 has a sawtooth shape including a sawtooth ridge 242 and a sawtooth trough 243, each of the sawtooth ridge 242 and the sawtooth trough 243 is provided in twelve to be at constant intervals, the sawtooth ridge 242 has a diameter of 16 mm, the sawtooth trough 243 has a diameter of 11 mm, and the discharge tip 240 has a whole thickness of 0.8 mm.

The gravel circulation dry electrostatic precipitator, in which a through-hole 241 into which the discharge rod 230 is inserted passes through the discharge tip 240, the discharge tip 240 has an outer circumferential surface in which recessed portions 245 are defined, the recessed portions 24 each have both ends, and the ends thereof are in contact with each other to have a peak 246 shape.

The gravel circulation dry electrostatic precipitator, in which the corona reaction part 22 comprises a titanium dioxide $TiO_2$ that is a deodorizing catalyst, and the titanium dioxide is activated by electrons and photons generated during corona discharging to generate a hydroxyl radical for removing an odor-inducing substances.

The gravel circulation dry electrostatic precipitator, in which the deodorizing catalyst is provided by being mixed with a scoria that is a catalyst support, and the deodorizing catalyst is absorbed by or carried on the catalyst support."

Specific structural or functional descriptions for embodiments according to the concept of the present invention disclosed in this specification are merely exemplified for purposes of describing the embodiments according to the concept of the invention. Thus, embodiments of the present invention are susceptible to various modifications and alternative forms, and cover all modifications, equivalents, and alternatives falling within the spirit and scope of the invention. Moreover, terms or words used in this specification and claims should not be restrictively interpreted as ordinary meanings or dictionary-based meanings, but should be interpreted as meanings and concepts conforming to the scope of the present invention on the basis of the principle that an inventor can properly define the concept of a term to describe and explain his or her invention in the best ways. Therefore, the embodiments described in this specification and the constructions illustrated in the drawings are only preferred embodiments of the present invention, and may not describe the technical spirit thoroughly. Accordingly, it should be understood that various equivalents and modifications which can substitute the embodiments may be provided at a point of application time of this specification.

Unless otherwise defined, all terms including technical and scientific terms used herein have the same meaning as commonly understood by one of ordinary skill in the art to which this invention belongs. Terms as defined in a commonly used dictionary should be construed as having the same meaning as in an associated technical context, and unless defined apparently in the description, the terms are not ideally or excessively construed as having formal meaning.

Hereinafter, a gravel circulation dry electrostatic precipitator according to the present invention will be described in detail with reference to the accompanying drawings.

Figure 2:
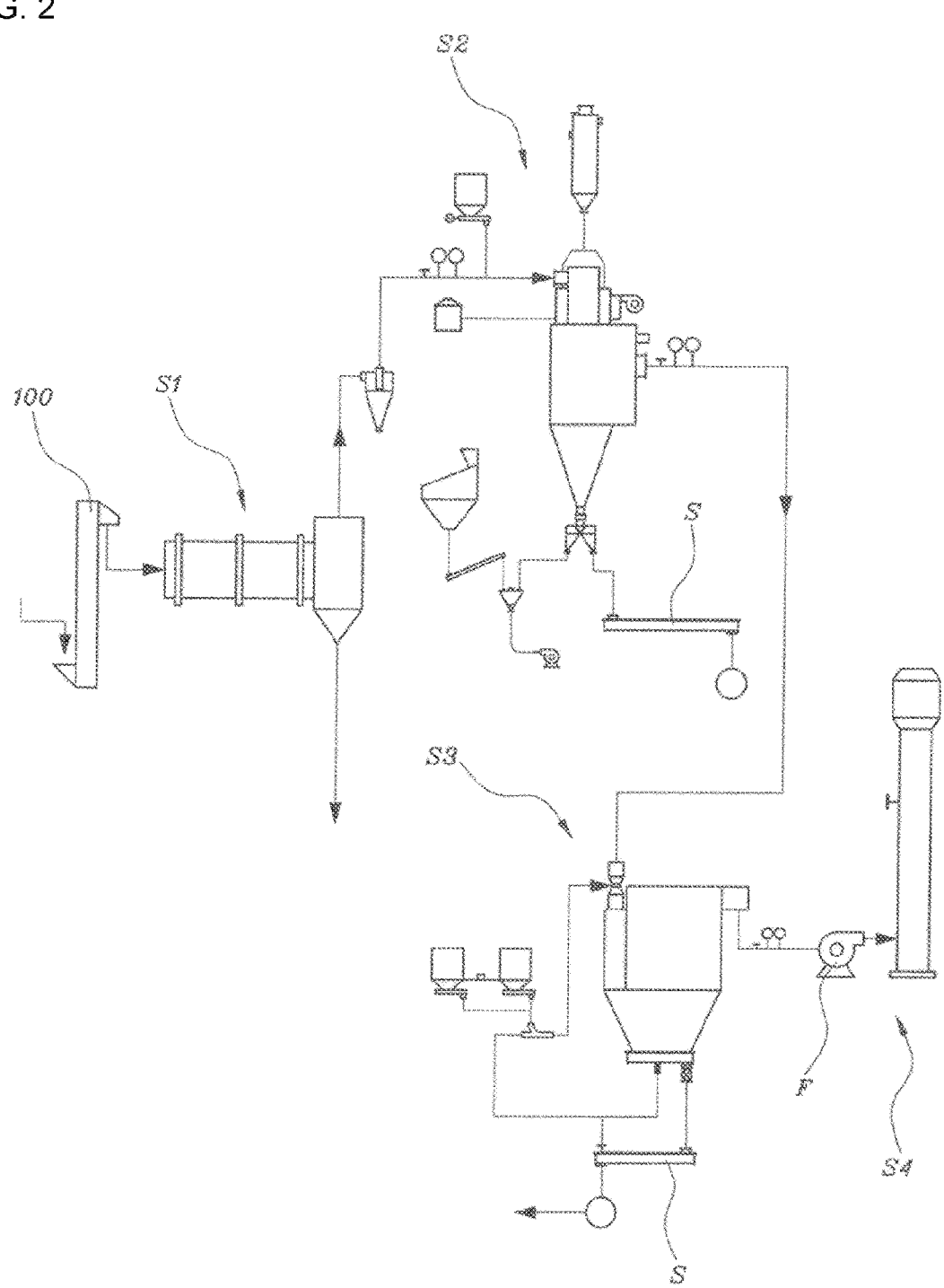
FIG. 2 is a schematic view illustrating a dust collection process for an aggregate in a gravel circulation dry electrostatic precipitator according to the present invention.
Figure 3:
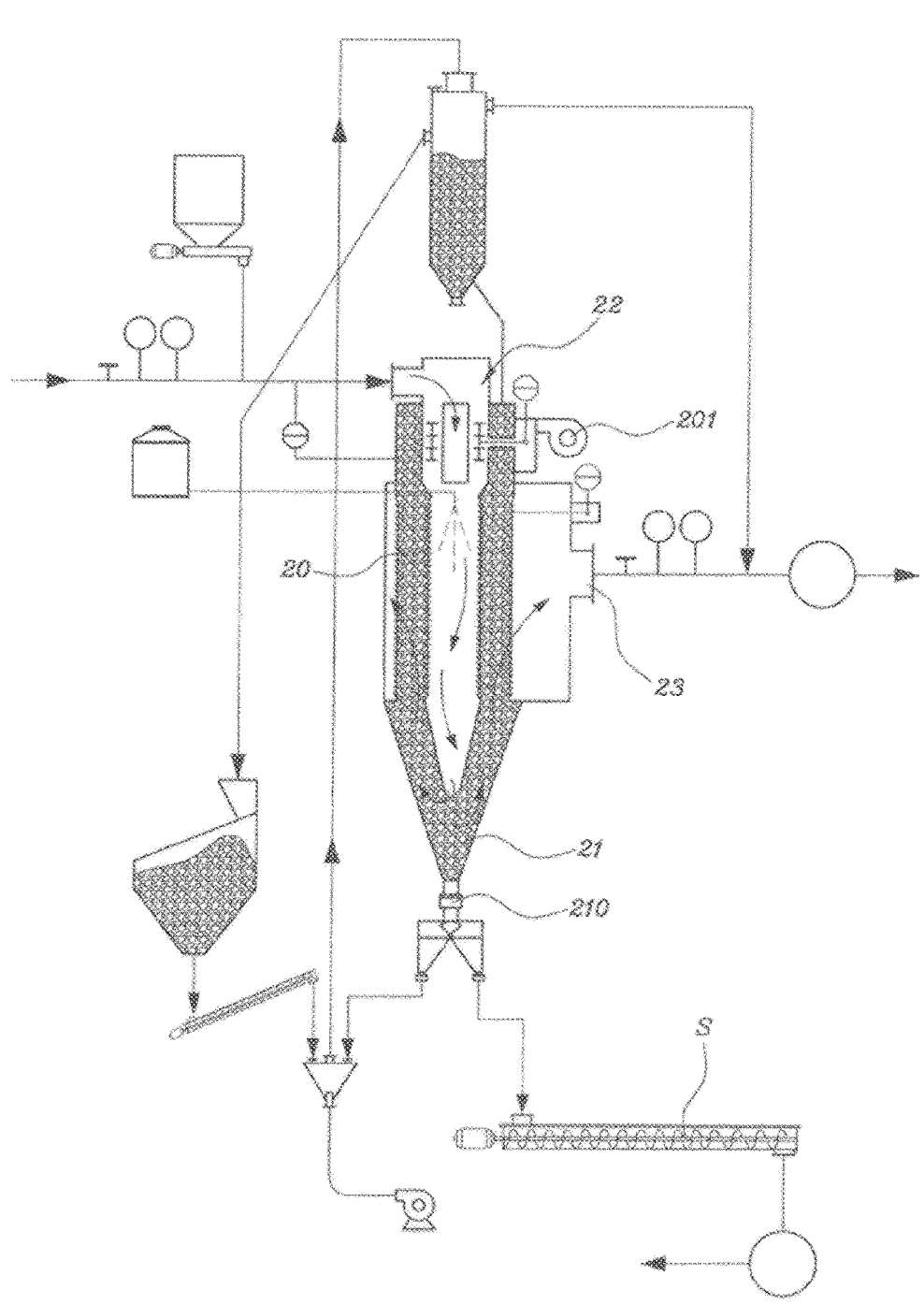
FIG. 3 is a detailed view of a first dust collection and purification unit of a gravel circulation dry electrostatic precipitator according to the present invention.
Figure 4:
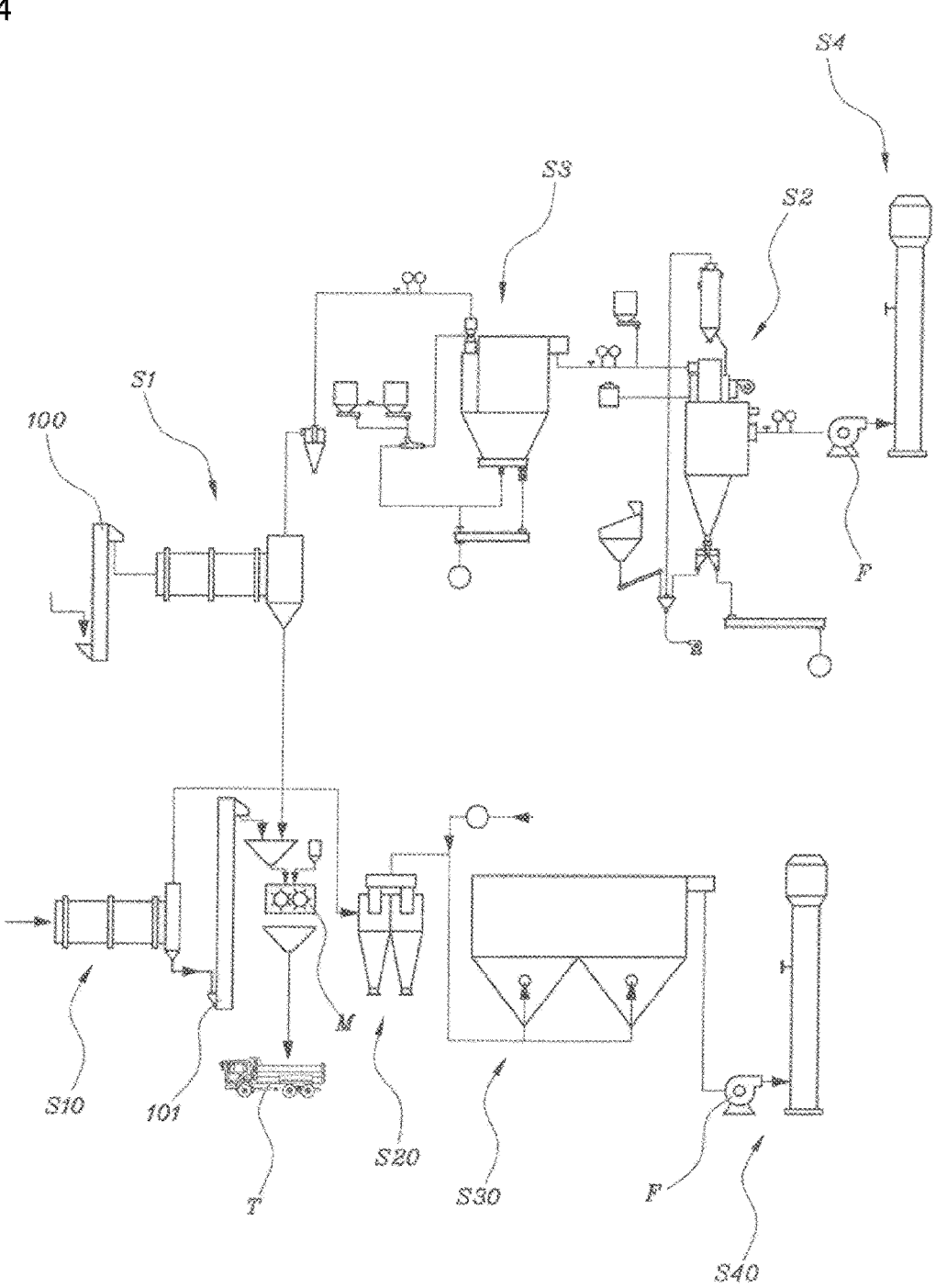
FIG. 4 is a schematic view illustrating an operation in which a second dust collection and purification unit collects and purifies dust, and then a first dust collection and purification unit collects and purifies the dust in a gravel circulation dry electrostatic precipitator according to another embodiment of the present invention.
Figure 5:
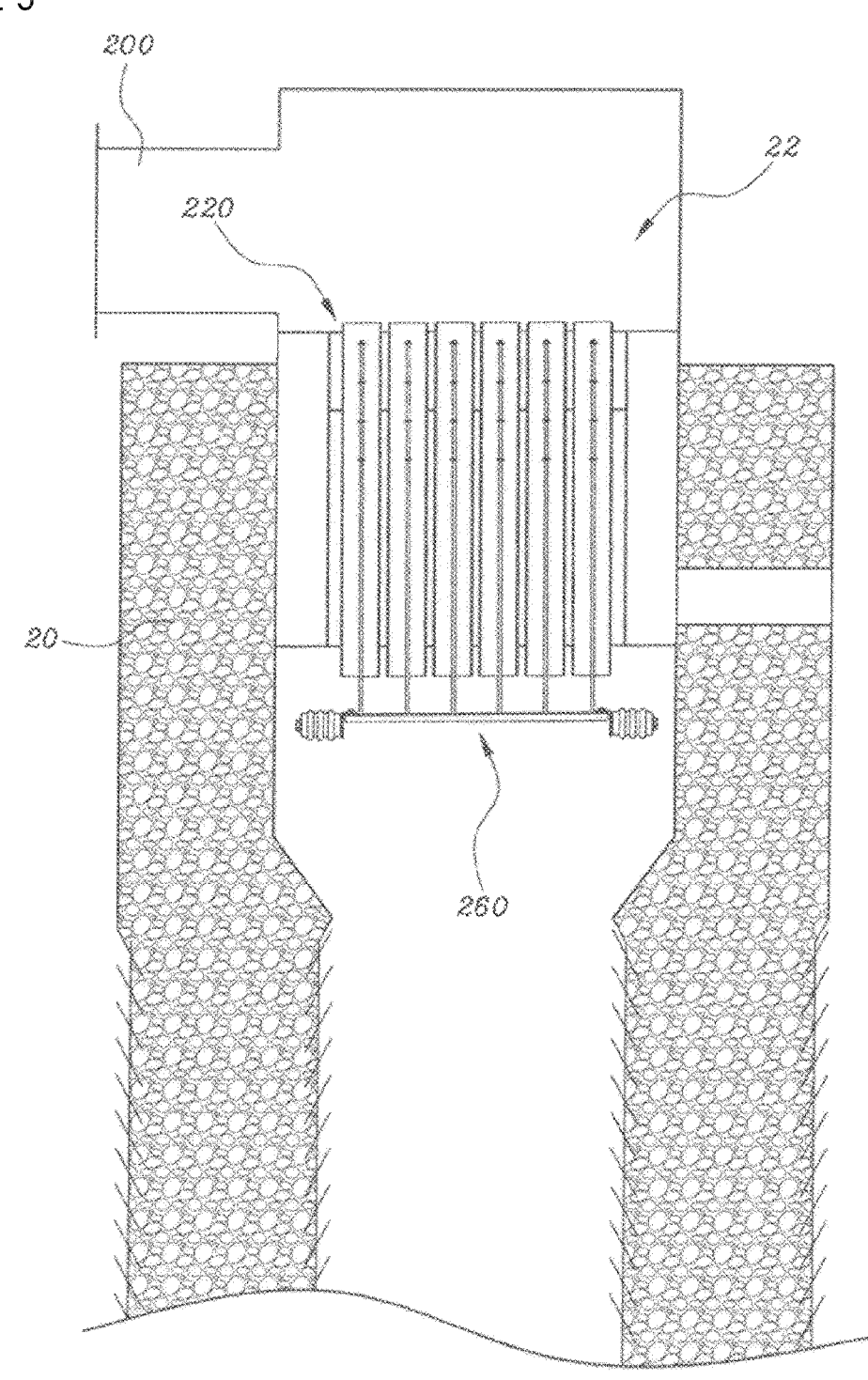
FIG. 5 is a cross-sectional view of a corona reaction part of a gravel circulation dry electrostatic precipitator according to the present invention.
Figure 6:
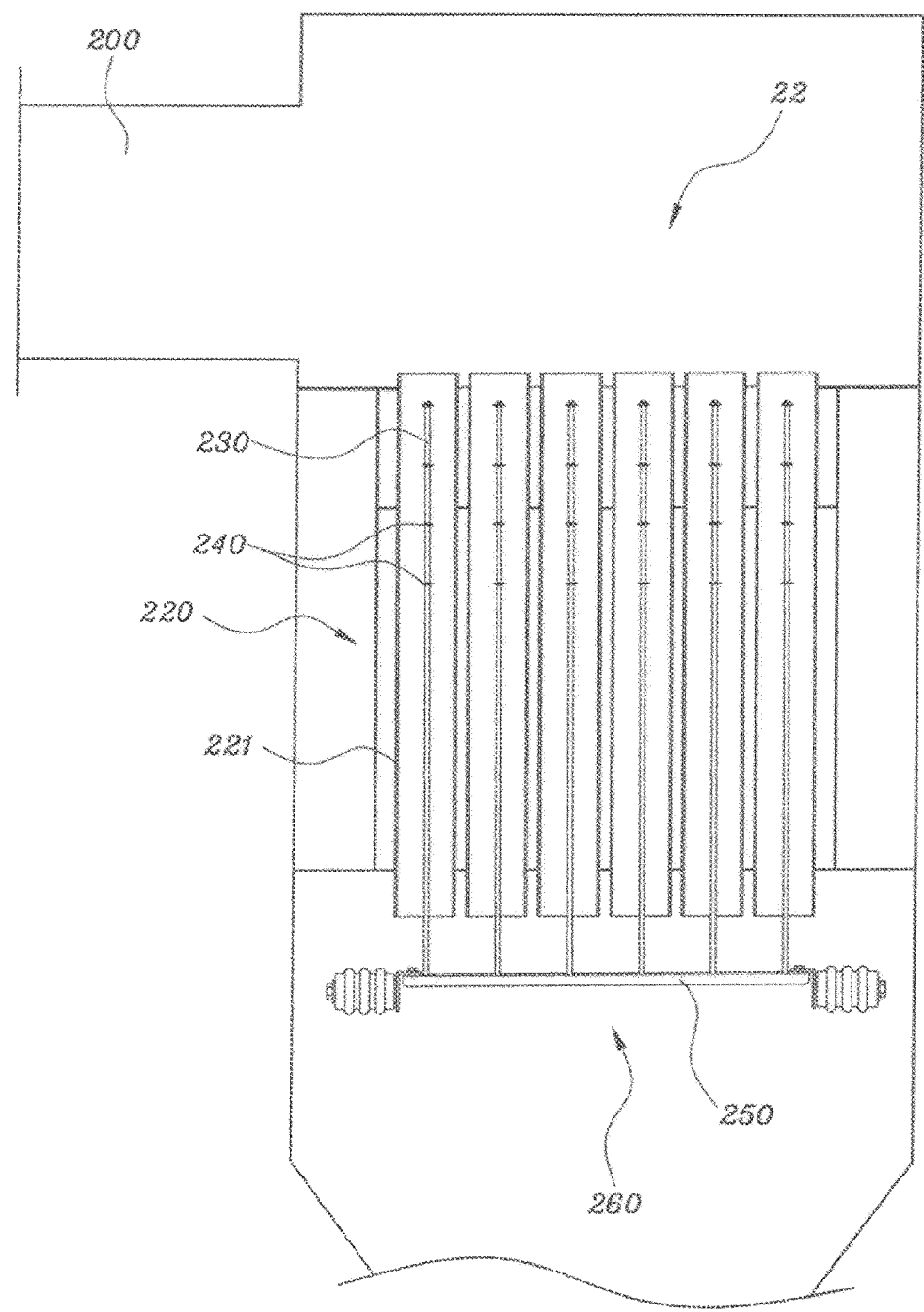
FIG. 6 is an enlarged view of a corona reaction part of a gravel circulation dry electrostatic precipitator according to the present invention.
Figure 7:
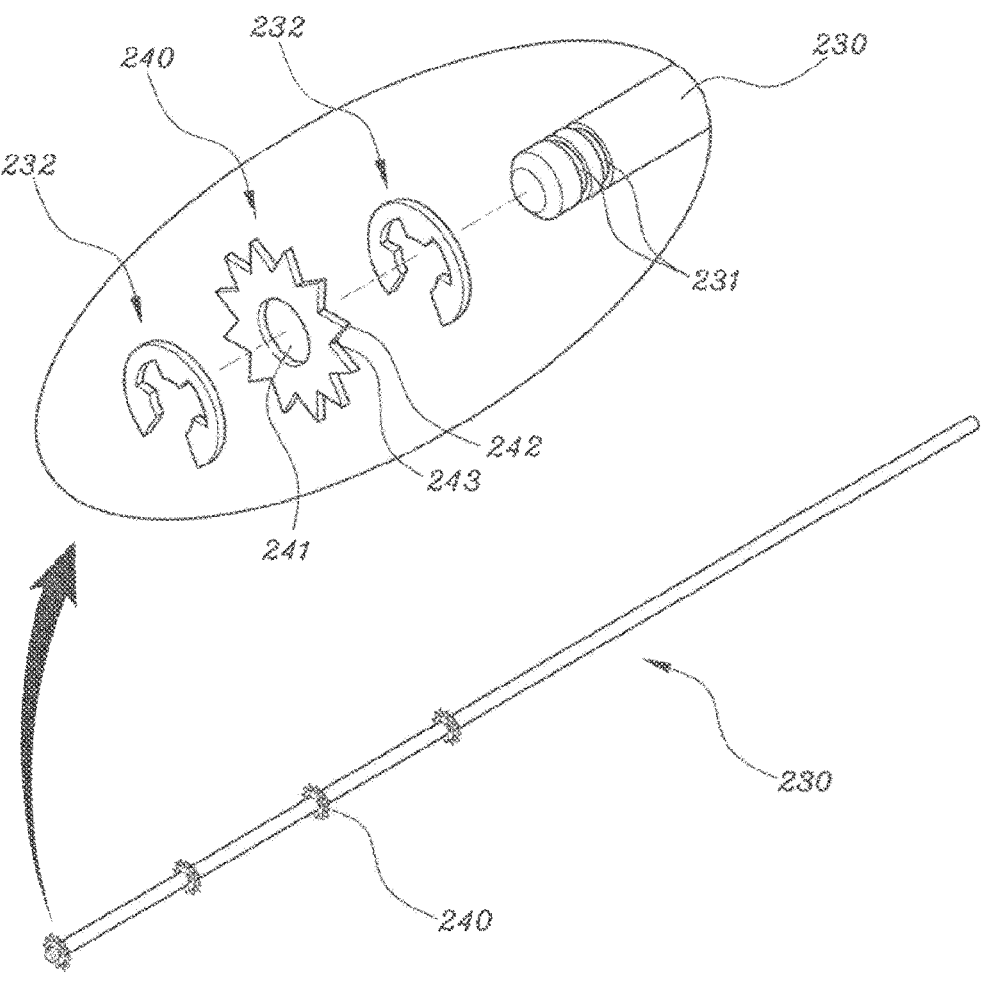
FIG. 7 is a main perspective view illustrating a discharge rod and a discharge tip of a gravel circulation dry electrostatic precipitator according to the present invention.
Figure 8:
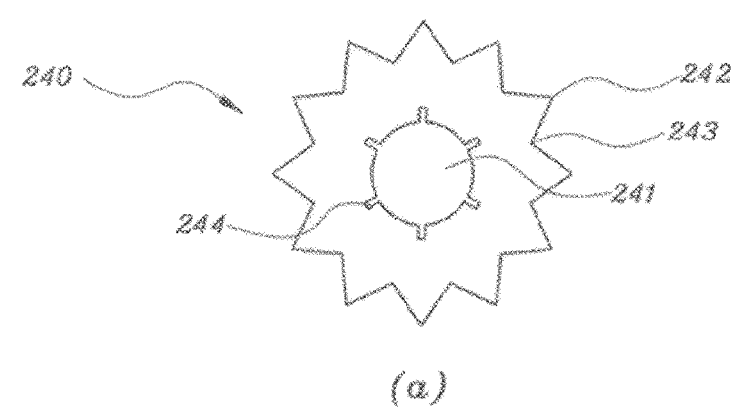
FIG. 8 is a view illustrating shapes of discharge tips according to various embodiments of the present invention.
Figure 8:
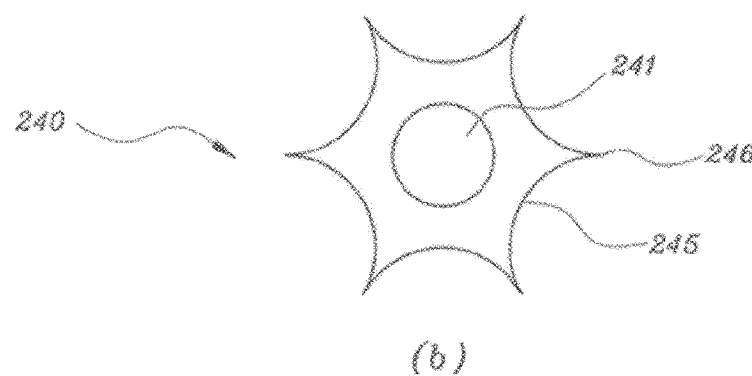
Figure 8:
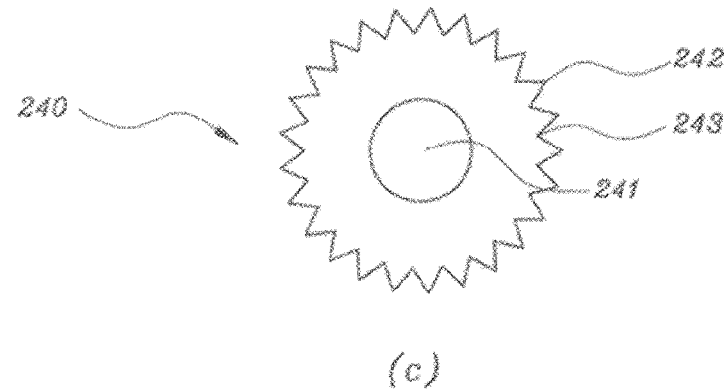

FIG. 1 is an overall schematic view of a gravel circulation dry electrostatic precipitator according to the present invention. FIG. 2 is a schematic view illustrating a dust collection process for an aggregate in a gravel circulation dry electrostatic precipitator according to the present invention. FIG. 3 is a detailed view of a first dust collection and purification unit of a gravel circulation dry electrostatic precipitator according to the present invention. FIG. 4 is a schematic view illustrating an operation in which a second dust collection and purification unit collects and purifies dust, and then a first dust collection and purification unit collects and purifies the dust in a gravel circulation dry electrostatic precipitator according to another embodiment of the present invention. FIG. 5 is a cross-sectional view of a corona reaction part of a gravel circulation dry electrostatic precipitator according to the present invention. FIG. 6 is an enlarged view of a corona reaction part of a gravel circulation dry electrostatic precipitator according to the present invention. FIG. 7 is a main perspective view illustrating a discharge rod and a discharge tip of a gravel circulation dry electrostatic precipitator according to the present invention. FIG. 8 is a view illustrating shapes of discharge tips according to various embodiments of the present invention.

As illustrated in FIG. 1, in specific components according to the present invention, an apparatus for removing odor-inducing substances, harmful gases, dust, and the like generated from a recycled aggregate, and includes a drying unit S1, a first dust collection and purification unit S2, a second dust collection and purification unit S3, and a discharge unit S4, and an apparatus for removing odor-inducing substances, harmful gases, dust, and the like generated from a new aggregate, and includes a drying unit S10, a first purification unit S20, a second purification unit S30, and a discharge unit S40, are provided in a batch manner, and in a time-series manner.

As illustrated in FIG. 1, as relatively less odor-inducing substances, harmful gases, dust, and the like are in the new aggregate unlike the recycled aggregate, the new aggregate is conveyed to the drying unit S10 using a bucket elevator 101, and then heated and dried. The Odor-inducing substances, the harmful gases, the dust, and the like generated from the dried new aggregate pass through the first purification unit S20 and the second purification unit S30 in sequence, and then, purified air is discharged to the outside through the discharge unit S40 by using a turbo fan F, and remaining new aggregate, i.e., the odor-inducing substances, the harmful gases, the dust, and the like, are forcibly suctioned and conveyed to the first purification unit S20. Then, the dried new aggregate is mixed with the recycled aggregate to be described below at a fixed ratio in a mixing unit M, and then is discharged to the outside by using a truck T.

As illustrated in FIGS. 1 and 2, the drying unit S1 is a unit that is disposed at one side and conveys the recycled aggregate, from which odor-inducing substances, harmful gases, dust, and the like are generated, by using a bucket elevator 100 to uniformly mix, heat, and dry the recycled aggregate.

The recycled aggregate is dried as above, and the odor-inducing substances, harmful gases, and dust generated from the dried recycled aggregate are forcibly suctioned into the first dust collection and purification unit S2 to be described below. The remaining recycled aggregate is mixed with the new aggregate separately dried by the drying unit S10 at a fixed ratio in the mixing unit M, and then is discharged to the outside by using the truck T.

Then, as illustrated in FIGS. 1 to 3, the odor-inducing substances, harmful gases, and dust generated in the drying unit S1 are forcibly suctioned through a pipe provided at an upper side, to be conveyed to the first dust collection and purification unit S2. The first dust collection and purification unit S2 includes a gravel accommodation part 20 including an inlet 200 on one side thereof and a blower fan 201 on the other side, and having an inner circumferential wall surface on which gravel is accommodated, a gravel collecting part 21 disposed on a lower end of the gravel accommodation part 20 and including a discharge valve 210 through which the gravel is replaced, a corona reaction part 22 disposed at a center of an upper inner circumferential portion of the first dust collection and purification unit, and an outflow part 23 which is disposed on one side of the gravel accommodation part 20 and through which the purified air flows out.

As above, when the odor-inducing substances, harmful gases, and dust generated in the drying unit S1 are forcibly suctioned through the pipe provided at the upper side into the first dust collection and purification unit S2, i.e., introduced through the inlet 200, the odor-inducing substances, the harmful gases, the dust, and the like are primarily removed in the corona reaction part 22. Here, the blower fan 201 serves to perform cleaning to prevent foreign matters from being attached to a discharge tip and a discharge rod, which are components of the corona reaction part 22, so as not to interrupt the removal of the odor-inducing substances, the harmful gases, the dust, and the like. Hereinafter, this corona reaction part 22 will be specifically described.

As illustrated in FIGS. 5 and 6, the corona reaction part 22 includes a dust collector 220 in which a plurality of dust collecting pipes 221 are accommodated, and a discharge unit 260 including a discharge rod 230 accommodated inside each of the dust collecting pipes 221 of the dust collector 220, discharge tips 240 coupled to a front end of the discharge rod 230 so as to be spaced a certain distance from each other, and a high-voltage applying device 250 that applies a voltage to an end of the discharge rod 230.

As illustrated in FIG. 7, the dust collecting pipe 221 has an outside diameter of 76.3 mm, an inside diameter of 74.5 mm, a thickness of 0.9 mm, and a length of 497 mm. A through-hole 241 into which the discharge rod 230 is inserted passes through the discharge tip 240 of the discharge unit 260. An outside of the discharge tip 240 has a sawtooth shape including a sawtooth ridge 242 and a sawtooth trough 243, and each of the sawtooth ridge 242 and the sawtooth trough 243 is provided in twelve to be at constant intervals. The sawtooth ridge 242 has a diameter of 16 mm, the sawtooth trough 243 has a diameter of 11 mm, and the discharge tip has a whole thickness of 0.8 mm.

A fixing groove 231 is defined in the discharge rod 230 so that each of fixing rings 232 is fixed to the fixing groove 231. The discharge tip 240 is seated between the fixing rings 232, and consequently, the discharge tip 240 is inserted into the discharge rod 230 so as to be fixed. The discharge tip 240 is provided in four to be installed to be spaced apart from each other starting from a front end of the discharge rod 230.

As illustrated in FIG. 8, a through-hole 241 into which the discharge rod 230 is inserted passes through the discharge tip 240. An outside of the discharge tip 240 has a sawtooth shape including a sawtooth ridge 242 and a sawtooth trough 243, and each of the sawtooth ridge 242 and the sawtooth trough 243 is provided in twelve to be at constant intervals. The sawtooth ridge 242 has a diameter of 16 mm, the sawtooth trough 243 has a diameter of 11 mm, the discharge tip has a whole thickness of 0.8 mm, and auxiliary through-holes 244 are defined in the through-hole 241 to extend to the outside, and are spaced a predetermined distance from each other.

A through-hole 241 into which the discharge rod 230 is inserted passes through the discharge tip 240. The discharge tip 240 has an outer circumferential surface in which recessed portions 245 are defined. The recessed portions 245 each have both ends, and the ends thereof are in contact with each other to have a peak 246 shape.

The corona reaction part 22 includes a titanium dioxide (TiO$_2$) that is a deodorizing catalyst, and the titanium dioxide is activated by electrons and photons generated during corona discharging to generate a hydroxyl radical for removing an odor causing substances.

The deodorizing catalyst is provided by being mixed with a scoria that is a catalyst support, and thus the deodorizing catalyst is absorbed by or carried on the catalyst support.

Figure 9:
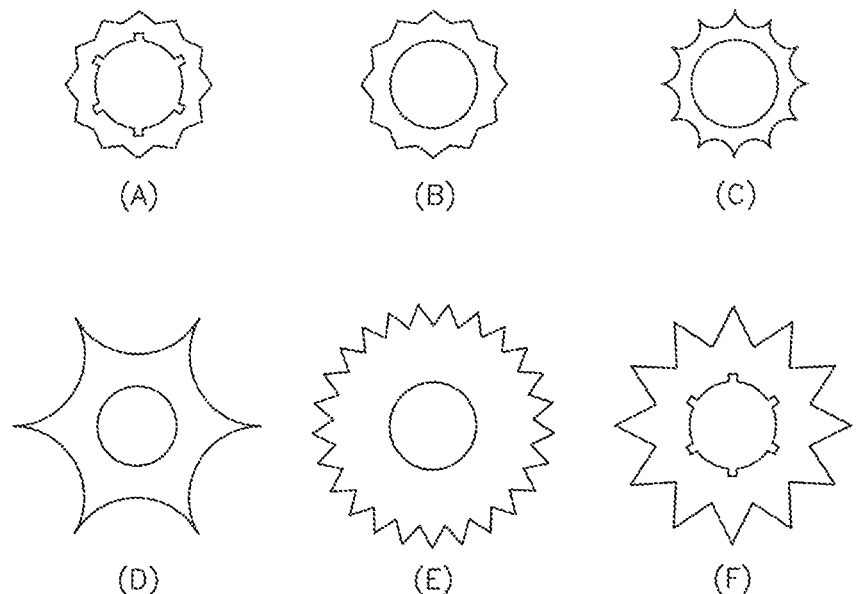
FIG. 9 is a view illustrating shapes of a discharge tips according to various embodiments of the present invention.
Figure 10:
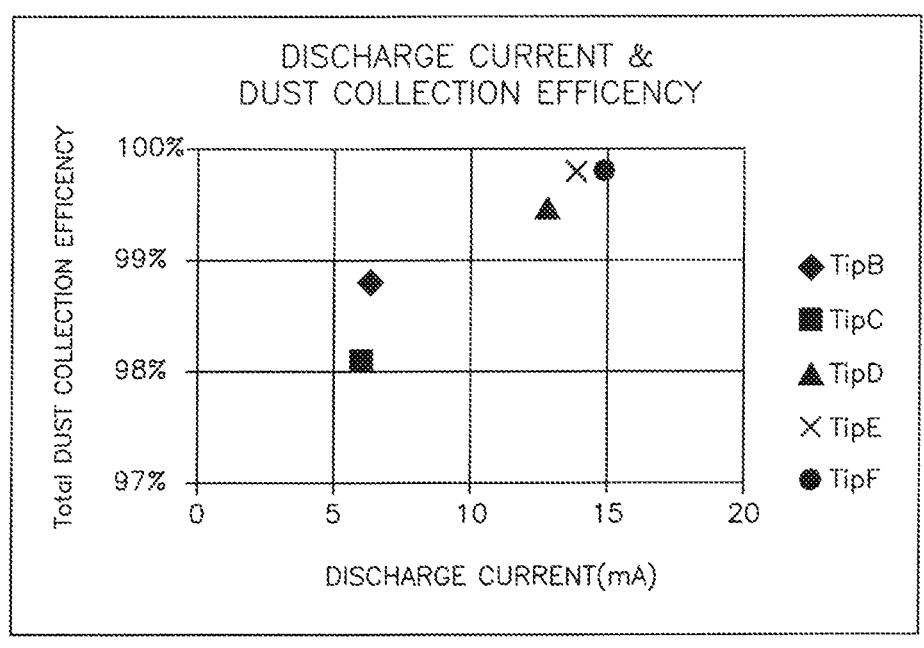
FIG. 10 is a table of experimental results of dust collection efficiency according to the various shapes of the discharge tips in FIG. 9 according to the present invention.

First, FIG. 9 illustrates shapes of discharge tips 240 according to various embodiments of the present invention. FIG. 10 show experimental results of dust collection efficiency according to the various shapes of the discharge tips 240.

As shown above, it was confirmed through the experiment that among the shapes of the discharge tips 240, a shape F is the most superior in dust collection efficiency. Based on these results, each of the discharges tip 240 was provided to have a sawtooth shape including a sawtooth ridge 242 and a sawtooth trough 243, in which each of the sawtooth ridge 242 and the sawtooth trough 243 is provided in twelve to be at constant intervals, the sawtooth ridge 242 has a diameter of 16 mm, the sawtooth trough 243 has a diameter of 11 mm, and the discharge tip has a whole thickness of 0.8 mm.

Here, although the shape of the discharge tip 240 was provided as the shape F through the experiment as above, the discharge tips 240 having shapes A, B, C, D, and E may be selectively used according to shapes of the dust collecting pipe 221 and the discharge rod 230, and it can be said that these shapes are also in the scope of the right of the present invention.

As above, the shapes of the discharge tip 240 were obtained through the experiment, and then various experiments were performed to find an embodiment that is the most superior in dust collection efficiency in disposing the discharge tips 240 on the discharge rod 230.

Figures 11, 12:
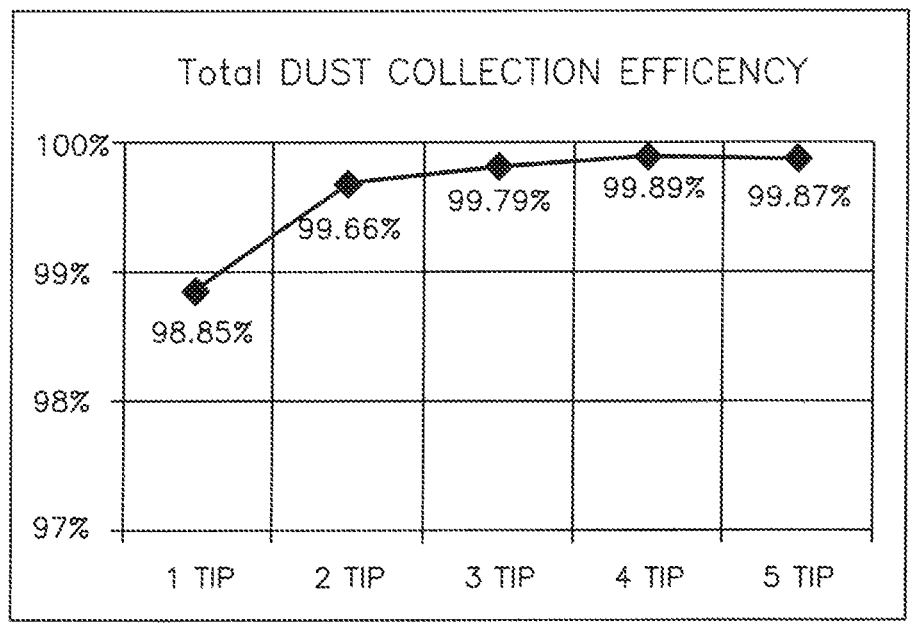
FIG. 11 is a table of experimental results of dust collection efficiency according to the number of a discharge tip according to the present invention.
FIG. 12 is a table showing results of discharge current, specific current, and power efficiency according to an arrangement distance between discharge tips according to the present invention.

First, FIG. 11 shows experimental results of dust collection efficiency according to the number of the discharge tips 240.

As shown above, as a result of an experiment of discharge current and dust collection efficiency according to the discharge tips 240, a phenomenon, in which the dust collection efficiency increased according to the number, but was halted at a certain section, was confirmed. Through this experiment, it was confirmed that as the number of the discharge tips 240 increases, the dust collection efficiency does not increase indefinitely.

It was confirmed through this experiment that a difference in result between a case in which one discharge tip 240 was installed and cases in which four to five discharge tips 240 were installed were very great, but a difference in result value between the cases of installing four discharge tips 240 and five discharge tips 240 was not great. Based on these results, the number of the discharge tips 240 was preferentially set to four when determining the number of the discharge tip 240. In the following experiment, an experiment was performed on effects of a distance between the discharge tips 240 on the dust collection efficiency.

Here, the experiment was performed by setting arrangement distances between the discharge tips 240 to 30 mm, 60 mm, and 90 mm, and coupling the discharge tips 240 to the discharge rod 230 starting from an end of the discharge rod

Figure 13:
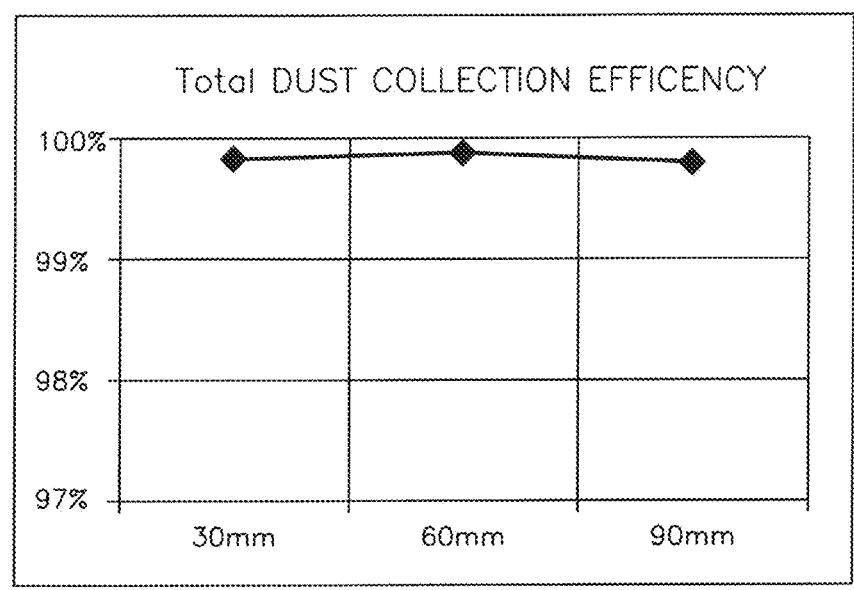
FIG. 13 is a table showing results of total dust collection efficiency in FIG. 12 according to the present invention.

230. This experiment was performed to confirm changes in dust collection efficiency according to lengths of a section of the discharge tip 240, on which pollutant particles are charged, and a collection section on which pollutant particles are collected, and a coupling distance for the discharge tips 240 determined based on the previous experiments of the number and the shape of the discharge tips 240 is determined. And results as illustrated in FIGS. 12 and 13 could be obtained.

As shown above, it was expected that as a result of measuring the dust collection efficiency according to the distances between the discharge tips 240, the distance of 60 mm in which the measured discharge current value was the greatest, would show the highest dust collection efficiency, and the distance of 30 mm would show the lowest dust collection efficiency. However, the actual experimental result shows that the distance of 60 mm showed the highest dust collection efficiency, and the distance of 90 mm showed the lowest dust collection efficiency. This reason was confirmed to be due to a phenomenon shown because as the section of the discharge tip 240, on which pollutant particles are charged, is increased, an effective length of the pollutant particle collecting section positioned thereafter is decreased, and thus not enough to achieve sufficient dust collection. In this regard, an experiment according to the effective length of the collecting section was additionally performed. Through an experiment of the proper distance between the discharge tips 240, and the effective length of the collecting section to achieve sufficient dust collection, it was confirmed that a case, in which the distance between the discharge tips 240 is set to 75 mm that is a median value of 60 mm and 90 mm, is the most superior in dust collection efficiency.

As above, the odor-inducing substances, the harmful gases, the dust, and the like are primarily removed in the corona reaction part 22, and then the odor-inducing substances, the harmful gases, the dust, and the like are secondarily purified by gravel accommodated in the gravel accommodation part 20. Thereafter, the purified air flows out through the outflow part 23.

In the method for purifying the odor-inducing substances, the harmful gases, the dust, and the like by gravel accommodated in the gravel accommodation part 20, the odor-inducing substances, the harmful gases, the dust, and the like are forcibly suctioned through the turbo fan F provided in the discharge unit S4 so that a vortex phenomenon is generated in the first dust collection and purification unit S2. Consequently, the odor-inducing substances, the harmful gases, the dust, and the like are in contact and collide with the gravel accommodated in the gravel accommodation part 20, and accordingly, are reduced to powder or adsorbed by the gravel so that the odor-inducing substances, the harmful gases, the dust, and the like are removable.

When the gravel having collided with and adsorbed the odor-inducing substances, the harmful gases, the dust, and the like, is discharged through the discharge valve 210 provided in a lower end of the gravel collecting part 21 so as to be replaced, the gravel is discharged by using a screw S, and moves to an upper side of the first dust collection and purification unit S2 to be filled.

Then, as illustrated in FIGS. 1 and 2, the odor-inducing substances, the harmful gases, and the dust having passed through the first dust collection and purification unit S2 flow out through the outflow part 23 to be introduced into the second dust collection and purification unit S3 in which fine dust, remaining after the odor-inducing substances, the harmful gases, and the dust are filtered by a filter, is discharged to the outside by the screw S provided at the lower end of a hopper, so that the odor-inducing substances, the harmful gases, and the dust are finally purified.

Thereafter, fresh air passing through the second dust collection and purification unit S3 is forcibly suctioned through the turbo fan F, and the purified air is discharged through the outlet 400 of the discharge unit S4.

As illustrated in FIG. 4, the second dust collection and purification unit S3 and the first dust collection and purification unit S2 may switch the order so as to enable purification through the drying unit S1, the second dust collection and purification unit S3, and then the first dust collection and purification unit S2.

The present invention as described above may be installed in incinerators, boilers, desulfurization equipment, and other microscopic dust and harmful gas removing equipment in various industrial settings. Thus, microscopic dust and harmful gases included in discharged gases, and particularly microscopic dust and harmful gases generated during the process for producing ascon may be removed or minimized using one batch apparatus to prevent environmental pollution. In addition, a principle in which ions, radicals, ozone, and the like generated during electric discharge decompose and remove substances such as sulfur dioxide, nitrogen oxide, and dioxin, contained in air pollutants, may be used to rapidly remove a large amount of air pollutants.

In addition, discharge voltages and discharge current values are optimized through the experiments of the shapes of the discharge tips and the distance between the discharge tips to be disposed on the discharge rod. Thus, a correlation between the dust collection efficiency and the power efficiency may be demonstrated, and an optimum specification may be derived to expect an effect of being capable of maximizing the dust collection efficiency.

In addition, according to the present invention, an occurrence of sparks may be greatly reduced to secure operation reliability. Accordingly, due to the reduction in occurrence of the sparks, lifetime of power supply may be increased to expect an effect that the lifetime increases.

In addition, according to the present invention, each of the dust collecting pipes is capable of being separated individually to be cleaned using brush. Accordingly, a cleaning operation may be easily performed to expect an effect that convenience is greatly increased in terms of maintenance.

Although the present invention has been described with reference to the limited embodiments and drawings, the present invention is not limited thereto and may be variously implemented by those of ordinary skill in the art to which the present invention pertains, within the technical idea of the present invention and an equivalent of the appended claims.

Therefore, the scope of the present invention should be defined based on the appended claims, and its modifications and equivalents should also be regarded as falling into the scope of the present invention.

The invention claimed is:

1. A gravel circulation dry electrostatic precipitator comprising:

a drying unit (S1) configured to convey a recycled aggregate, which contains a large amount of moisture, among materials of asphalt-concrete (ascon) by using a bucket elevator (100) to uniformly mix, heat, and dry the aggregate;

a first dust collection and purification unit (S2) configured to forcibly suction odor-inducing substances, harmful gases, and dust, which are generated in the drying unit (S1), through a pipe provided on an upper side to collect and purify the odor-inducing substances, the harmful gases, and the dust;

a second dust collection and purification unit (S3) in which fine dust, remaining after the odor-inducing substances, the harmful gases, and the dust that have passed through the first dust collection and purification unit (S2) are filtered by a filter, is discharged to the outside by a screw (S) provided at a lower end of a hopper; and a discharge unit (S4) configured to forcibly suction fresh air, which has passed through the second dust collection and purification unit (S3), by using a turbo fan (F) to discharge the fresh air through an outlet (400), wherein the first dust collection and purification unit (S2) comprises:

a gravel accommodation part (20) comprising an inlet (200) on one side thereof and a blower fan (201) on the other side, and having an inner circumferential wall surface on which gravel is accommodated;

a gravel collecting part (21) disposed on a lower end of the gravel accommodation part (20) and comprising a discharge valve (210) through which the gravel is replaced;

a corona reaction part (22) provided at a center of an upper inner circumferential portion of the first dust collection and purification unit; and an outflow part (23) which is disposed on one side of the gravel accommodation part (20) and through which the purified air flows out, wherein the corona reaction part (22) comprises:

a dust collector (220) in which a plurality of dust collecting pipes (221) are accommodated; and a discharge unit (260) comprising a discharge rod (230) accommodated inside each of the dust collecting pipes (221) of the dust collector (220), discharge tips (240) coupled to a front end of the discharge rod (230) so as to be spaced a constant distance from each other, and a high-voltage applying device (250) configured to apply a voltage to an end of the discharge rod (230), wherein a fixing groove (231) is defined in the discharge rod (230) so that each of fixing rings (232) is fixed to the fixing groove (231), the discharge tip (240) is seated between the fixing rings (232) so that the discharge tip (240) is inserted into the discharge rod (230) so as to be fixed, and the discharge tip (240) is provided in four to be installed to be spaced 75 mm from each other starting from a front end of the discharge rod (230), wherein, in the discharge tip (240), a through-hole (241) into which the discharge rod (230) is inserted passes through the discharge tip (240), an outside of the discharge tip (240) has a sawtooth shape comprising a sawtooth ridge (242) and a sawtooth trough (243), each of the sawtooth ridge (242) and the sawtooth trough (243) is provided in twelve to be at constant intervals, the sawtooth ridge (242) has a diameter of 16 mm, the sawtooth trough (243) has a diameter of 11 mm, the discharge tip (240) has a whole thickness of 0.8 mm, and auxiliary through-holes (244) are defined in the through-hole (241) to extend to the outside, and are spaced a predetermined distance from each other.

2. The gravel circulation dry electrostatic precipitator of claim 1, wherein the odor-inducing substances, harmful gases, and dust generated from the dried recycled aggregate passing through the drying unit (S1) are forcibly suctioned into the first dust collection and purification unit (S2), and the remaining recycled aggregate is mixed with a new aggregate separately dried by a drying unit (S10) at a fixed ratio in a mixing unit (M), and then is discharged to the outside by using a truck (T).

3. The gravel circulation dry electrostatic precipitator of claim 1, wherein the dust collecting pipe (221) has an outside diameter of 76.3 mm, an inside diameter of 74.5 mm, a thickness of 0.9 mm, and a length of 497 mm, wherein a through-hole (241) into which the discharge rod (230) is inserted passes through the discharge tip (240) of the discharge unit (260), and an outside of the discharge tip (240) has a sawtooth shape comprising a sawtooth ridge (242) and a sawtooth trough (243), wherein each of the sawtooth ridge (242) and the sawtooth trough (243) is provided in twelve to be at constant intervals, the sawtooth ridge (242) has a diameter of 16 mm, the sawtooth trough (243) has a diameter of 11 mm, and the discharge tip (240) has a whole thickness of 0.8 mm.

4. The gravel circulation dry electrostatic precipitator of claim 1, wherein a through-hole (241) into which the discharge rod (230) is inserted passes through the discharge tip (240), and the discharge tip (240) has an outer circumferential surface in which recessed portions (245) are defined, wherein the recessed portions (245) each have both ends, and the ends thereof are in contact with each other to have a peak (246) shape.

5. The gravel circulation dry electrostatic precipitator of claim 1, wherein the corona reaction part (22) comprises a titanium dioxide ($TiO_2$) that is a deodorizing catalyst, wherein the titanium dioxide is activated by electrons and photons generated during corona discharging to generate a hydroxyl radical for removing an odor-inducing substances.

6. The gravel circulation dry electrostatic precipitator of claim 5, wherein the deodorizing catalyst is provided by being mixed with a scoria that is a catalyst support, wherein the deodorizing catalyst is absorbed by or carried on the catalyst support.

\* \* \* \* \*